(12) United States Patent
Kuang et al.

(10) Patent No.: US 12,203,079 B2
(45) Date of Patent: Jan. 21, 2025

(54) *AGROBACTERIUM*-MEDIATED GENETIC TRANSFORMATION METHOD FOR SEA BARLEYGRASS (71) Applicant: ZHEJIANG UNIVERSITY, Hangzhou (CN)

(72) Inventors: Liuhui Kuang, Hangzhou (CN); Qi Li, Hangzhou (CN); Dezhi Wu, Hangzhou (CN); Guoping Zhang, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 201 days.

(21) Appl. No.: 17/811,764

(22) Filed: Jul. 11, 2022

(65) Prior Publication Data

US 2023/0132082 A1  Apr. 27, 2023

(30) Foreign Application Priority Data

Oct. 25, 2021  (CN) .......................... 202111243915.1

(51) Int. Cl.
| | | |
|---|---|---|
| *C12N 15/82* | (2006.01) | |
| *A01H 1/04* | (2006.01) | |
| *A01H 4/00* | (2006.01) | |
| *A01H 6/46* | (2018.01) | |

(52) U.S. Cl.
CPC ........... *C12N 15/8205* (2013.01); *A01H 1/04* (2013.01); *A01H 4/008* (2013.01); *A01H 6/46* (2018.05)

(58) Field of Classification Search
None
See application file for complete search history.

(56) References Cited

U.S. PATENT DOCUMENTS

| | | | | |
|---|---|---|---|---|
| 2015/0079680 A1* | 3/2015 | Bradley | ................ | C12N 15/907 435/462 |
| 2017/0367280 A1* | 12/2017 | Hummel | ............ | C12N 15/8241 |

FOREIGN PATENT DOCUMENTS

| | | | | |
|---|---|---|---|---|
| CN | 107646681 A | * | 2/2018 | ............. A01H 4/001 |

OTHER PUBLICATIONS

Rotem-Abarbanell, Daphne, and Adina Breiman. "Plant regeneration from immature and mature embryo derived calli of Hordeum marinum." Plant cell, tissue and organ culture 16 (1989): 207-216. (Year: 1989).*

Ieamkhang, S., Chatchawankanphanich, O. Augmentin® as an alternative antibiotic for growth suppression of Agrobacterium for tomato (*Lycopersicon esculentum*) transformation. Plant Cell Tiss Organ Cult 82, 213-220 (2005). https://doi.org/10.1007/s11240-005-0416-6 (Year: 2005).*

Murashige, T. "Somatic plant cells." Tissue Culture. Academic Press, 1973. 170-172. (Year: 1973).*

GenBank Accession HM539475.1 "*Hordeum marinum* subsp. *marinum* isolate D64c hypothetical protein mRNA, partial cds" dated Jul. 25, 2016 www.ncbi.nlm.nih.gov/nucleotide/HM539475.1report=genbank &log$=nuclalign&blast_rank=1&RID=215TUMZS016 (Year: 2016).*

English translation of CN 107646681 A, published Feb. 2, 2018 (Year: 2018).*

Munns, R. and Tester, M., "Mechanisms of Salinity Tolerance", Annual Review of Plant Biology, 2008, 59, 651-681.

Timothy D. Colmer, Timothy J. Flowers, Rana Munns, "Use of wild relatives to improve salt tolerance in wheat", Journal of Experimental Botany, 2006, vol. 57, No. 5, pp. 1059-1078.

S. Islam, , A. I. Malik, A. K. M. R. Islam and T. D. Colmer, "Salt tolerance in a Hordeum marinum-Triticum aestivum amphiploid, and its parents", Journal of Experimental Botany, 2007, vol. 58, No. 5, pp. 1219-1229.

Hayta, S., Smedley, M.A., Demir, S.U et al. "An efficient and reproducible Agrobacterium-mediated transformation method for hexaploid wheat (*Triticum aestivum* L.)", Plant Methods, 2019, 15, 121.

Bartlett J G, Alves S C, Smedley M, et al., "High-throughput Agrobacterium-mediated barley transformation", Plant Methods, 2008, 4(1): 1-12.

* cited by examiner

*Primary Examiner* — Charles Logsdon
*Assistant Examiner* — Kelsey L McWilliams
(74) *Attorney, Agent, or Firm* — Hemisphere Law, PLLC; Zhigang Ma (57) ABSTRACT

An *Agrobacterium*-mediated genetic transformation method for sea barleygrass is provided. The method includes: S1, selecting immature embryo materials of sea barleygrass with immature embryos each having a length in a range of 0.5-1.0, sterilizing them with alcohol and sodium hypochlorite to obtain sterilized seeds; S2, separating the immature embryos, crosscutting the immature embryos, and inducing callus generation and proliferation; S3, adjusting pre-culture time and *Agrobacterium* infection time of calli based on the callus generation and *Agrobacterium* growth to thereby prevent excessive *Agrobacterium* liquid; and S4, performing adventitious bud induction culture and rooting induction culture under a shielding-formed low-light environment to obtain tissue culture plantlets. It relates to a tissue culture method for immature embryos of sea barleygrass with high green spot differentiation and plantlet formation rates, which is not limited by materials. A transformation and regeneration system has high genetic transformation and mutation efficiency.

11 Claims, 3 Drawing Sheets
Specification includes a Sequence Listing.

AGROBACTERIUM-MEDIATED GENETIC TRANSFORMATION METHOD FOR SEA BARLEYGRASS

TECHNICAL FIELD

The disclosure relates to the field of plant genetic engineering technologies, more particular to an *Agrobacterium*-mediated genetic transformation method for sea barleygrass.

SEQUENCE LISTING

This application incorporates by reference the material in the sequence listing submitted via an XML file titled 22041TBYX-USP1-SL.xml, with the data of creation being Jun. 24, 2024, and the size of the XML file being 10,709 bytes. No new matter is entered.

BACKGROUND

Tribe Triticeae provides the important cereal food crops in Poaceae, which produce up to 900 million tons annually, accounting for 30% of a total global cereal production. Soil salinization seriously restricts land use and crop production, and is one of the most important abiotic stresses in global agricultural production (Munns, R. and Tester, M., "Mechanisms of Salinity Tolerance", Annual Review of Plant Biology, 2008, 59, 651-681). Sea barleygrass (also referred to as *Hordeum marinum*) is a wild relative species of barley and wheat. It is the most salt-tolerant species in Triticeae and has a certain cross-ability with common wheat. Therefore, sea barleygrass is a potential gene donor for improving salt tolerance in wheat (Timothy D. Colmer, Timothy J. Flowers, Rana Munns, "Use of wild relatives to improve salt tolerance in wheat", Journal of Experimental Botany, 2006, 57, 1059-1078; S. Islam, A. I. Malik, A. K. M. R. Islam, and T. D. Colmer, "Salt tolerance in a *Hordeum marinum-Triticum aestivum* amphiploid, and its parents", Journal of Experimental Botany, 2007, 58, 5, 1219-1229). It is of great significance to clarify a specific molecular mechanism of salt tolerance in sea barleygrass for utilization of excellent genetic (e.g., gene) resources and improvement of salt tolerance in wheat. However, little progress has been made in the research on the salt tolerance mechanisms and the analysis of gene functions because of the lack of a genetic transformation system of sea barleygrass.

A genetic transformation system of Triticeae crops generally adopts a method of *Agrobacterium*-mediated transformation with immature embryos as explants, such as hexaploid wheat (Hayta, S., Smedley, M. A., Demir, S. U. et al. "An efficient and reproducible *Agrobacterium*-mediated transformation method for hexaploid wheat (*Triticum aestivum* L.)", Plant Methods, 2019, 15, 121) and barley (Bartlett J G, Alves S C, Smedley M, et al., "High-throughput *Agrobacterium*-mediated barley transformation", Plant Methods, 2008, 4: 1-12.). However, there is no report of a successful case in sea barleygrass, and the main reason is that a suitable regeneration system is available. The establishment of an efficient genetic transformation system can provide an effective way for further functional analysis of excellent salt-tolerant genes in sea barleygrass and their application in breeding.

SUMMARY

In view of this, it is necessary to aim at a current situation of a lack of a genetic transformation system of sea barleygrass, and a main purpose of the disclosure is to provide an *Agrobacterium*-mediated genetic transformation method for sea barleygrass. The method realizes a successful application of genetic transformation technology with a high transformation efficiency in sea barleygrass, and can be applied to gene function studies of sea barleygrass.

A main purpose of the disclosure is realized by technical solutions as follows.

Specifically, the disclosure provides an *Agrobacterium*-mediated genetic transformation method for sea barleygrass, including:

step S1, selection and sterilization of immature embryo materials of sea barleygrass, which includes: selecting the immature embryo materials of sea barleygrass, with the lengths of embryos being in a range of 0.5-1.0 millimeters (mm), and sterilizing them with alcohol and sodium hypochlorite to obtain sterilized seeds;

step S2, separation and callus induction of the immature embryos, which includes: separating the immature embryos from the sterilized seeds, crosscutting the immature embryos, and inducing callus generation and proliferation, thereby obtaining calli;

step S3, *Agrobacterium* infection and selective culture, which includes: adjusting pre-culture time and *Agrobacterium* infection time of the calli based on the callus generation and *Agrobacterium* growth to prevent excessive *Agrobacterium* liquid where a culture medium for the selective culture is added with Timentin™ (i.e., a mixture of ticarcillin and clavulanic acid) and hygromycin; and step S4, callus differentiation, plantlet formation, and positive plantlet detection, which includes: performing adventitious bud induction culture and rooting induction culture under a shielding-formed low-light environment to thereby obtain tissue culture plantlets, and then performing deoxyribonucleic acid (DNA) extraction and polymerase chain reaction (PCR) detection on the obtained tissue culture plantlets.

The disclosure provides the *Agrobacterium*-mediated genetic transformation method for sea barleygrass and a corresponding tissue culture system as follows.

In an embodiment, in the step S1, the selection and sterilization of immature embryo materials of sea barleygrass specifically includes: selecting the immature embryo materials of sea barleygrass with plump seeds, gelatinous endosperms, and translucent immature embryos each having the length in the range of 0.5-1.0 mm, retaining awns and keeping seed coats of the immature embryos materials to be intact; sterilizing the immature embryo materials of sea barleygrass with 70% alcohol, then soaking the sterilized immature embryos materials in a prepared sodium hypochlorite solution, and subsequently rinsing the soaked immature embryo materials repeatedly with sterilized water, to thereby obtain the sterilized seeds.

In an embodiment, in the step S2, the separation and callus induction of the immature embryos specifically includes:

taking the sterilized seeds obtained from the step S1, and placing the sterilized seeds on a petri dish (also referred to as culture dish) covered with a double-layer sterile filter paper, where a back of each of the sterilized seeds faces up and a tail of the awn faces away from an operator;

using a clamping method with tips of double pairs to pull off an entire back seed coat of each of the sterilized seeds to expose the whole immature embryos, where tips of a pair of left-hand tweezers of the double pairs of tweezers clamp the sterilized seed and tips of a pair of right-hand tweezers of the double pairs of tweezers tear the awn;

piercing ½ of an endosperm of each of the exposed immature embryos with the tips of the pair of left-hand tweezers and fixing the sterilized seed without the entire back seed coat, and obliquely pressing an upper of the endosperm of the immature embryo with the tips of the pair of right-hand tweezers to peel off the immature embryo, to thereby obtain peeled-off immature embryos;

placing the peeled-off immature embryos on a surface of a callus induction culture medium with fronts face upward, crosscutting middles of the peeled-off immature embryos one by one with the tips of one of the double pairs off tweezers; and culturing crosscut immature embryos in dark at 22° C. for 7 days, removing minor seedling buds with the tips of one of the double pairs off tweezers, continuing culturing in dark for 7 days, and then removing seedling buds and soft non-embryonic calli; and performing callus culture in dark for 2-3 weeks after replacing a new callus induction culture medium, to thereby obtain the calli;

where a subsequent operation is performed according to the step S3 when *Agrobacterium* infection is required to obtain transgenic plants;

where when the calli are directly used for the callus induction, yellow and dense embryogenic calli are taken from the calli obtain from the step S2 and cultured in dark at 22° C. for 3-4 weeks, a callus induction culture medium without hygromycin and the mixture of ticarcillin and clavulanic acid (Timentin™) is replaced every two weeks, and then a subsequent operation is performed according to the step S4.

In an embodiment, in the step S3, the *Agrobacterium* infection and selective culture specifically includes:

taking yellow and dense embryogenic calli from the calli obtained from the step S2, and pre-culturing taken yellow and dense embryogenic calli at 22° C. for 1 week, to thereby obtain pre-cultured callus blocks;

taking callus blocks each with a diameter of 2-3 mm from the pre-cultured callus blocks, using a 20 microliters (μL) pipettor to suck *Agrobacterium* liquid, dropwise adding sucked *Agrobacterium* liquid in middles of taken callus blocks to wrap the taken callus blocks, then immediately sucking back excess *Agrobacterium* liquid, placing a petri dish with the taken callus blocks on a clean bench in a tilted manner, and replacing a new callus induction culture medium after excess *Agrobacterium* liquid is dried, to thereby obtain infected callus blocks; and co-culturing the infected callus blocks for 36-48 hours, reducing a number of co-cultured callus blocks to 20-30 per petri dish, replacing two rounds of a callus induction screening culture medium, and culturing in dark for 3-4 weeks, to thereby obtain final co-cultured callus blocks.

In an embodiment, the *Agrobacterium* liquid employs a MG basic culture solution without antibiotic, and a concentration $OD_{600}$ (abbreviation for optical density at 600 nanometers) of the *Agrobacterium* liquid is in a range of 0.5-0.6.

In an embodiment, in the step S4, the callus differentiation, plantlet formation, and positive plantlet detection specifically includes:

covering a petri dish cover and a culture tube cover with single-layer A4 sized papers throughout in stages of the callus differentiation and the rooting induction culture since the calli are exposed to light, to thereby create the shielding-formed low-light environment;

taking yellow and dense callus blocks from the calli obtained in the step S2 or obtained in the step S3, 15-20 numbers of individual callus blocks per petri dish, and then culturing taken callus blocks for 2 weeks in a differentiation culture medium or a differentiation screening culture medium under the shielding-formed low-light environment;

removing whitish parts and soft textures of callus blocks, selecting small callus blocks with differentiated green spots, transferring selected callus blocks with the differentiated green spots to a new differentiation culture medium or a new differentiation screening culture medium, and then culturing for 2-4 weeks under the shielding-formed low-light environment;

when the differentiated green spots grow to be plantlets each with a length in a range of 2-3 centimeters (cm), transferring the plantlets to a rooting culture medium or a rooting screening culture medium, and then culturing for 2-3 weeks to form root systems of the plantlets;

when refining the plantlets, opening the culture tube cover, adding sterilized water to 1-2 cm above a liquid level, adapting to 1-2 days in an external environment, rinsing the rooting culture medium or the rooting screening culture around the root systems with tap water, and then culturing rinsed plantlets in a ⅕ Hogland hydroponic culture medium for 3-4 weeks, to thereby obtain the tissue culture plantlets;

performing the DNA extraction and the PCR detection on the tissue culture plantlets to obtain PCR detection results, and determining target fragments whether are amplified based on the PCR detection results, to thereby determine the detected tissue culture plantlets whether are positive plantlets;

where the callus differentiation and the plantlet formation are performed after transformation, the differentiation screening culture medium and the rooting screening culture medium are used; and where when an *Agrobacterium tumefaciens* recombinant strain used for transformation carries a gene editing vector, performing PCR amplification on a sequence near a target of each of the positive plantlets, and detecting mutation sites by Sanger sequencing.

In an embodiment, a dosage of the hygromycin maintains an initial dosage in a stage of the callus induction, and then is gradually reduced in a stage of the callus differentiation and in a stage of the rooting induction culture.

In an embodiment, a Murashige and Skoog (MS) culture medium is used as a basic culture medium for each culture medium described in the steps S2-S4, and ingredients in 1 L (liter) include:

a, the callus induction culture medium, including: 4.3 grams (g) MS basic culture medium without vitamin, 30 g maltose, 1.0 g casein hydrolysate, 690 micrograms (mg) proline, 350 mg inositol, 1.0 mg thiamine hydrochloride, 5 mg dicamba, 1.25 mg copper sulfate pentahydrate ($CuSO_4 \cdot 5H_2O$), 3.65 g plant gel, and adjusted to pH=5.8 with 1 Mole per liter (M) sodium hydroxide (NaOH);

the callus induction screening culture medium, including: the callus induction culture medium, 200 mg the mixture of ticarcillin and clavulanic acid (Timentin™), and 25 mg hygromycin;

b, the differentiation culture medium, including: 2.7 g MS culture basic medium without ammonium nitrate ($NH_4NO_3$) and vitamin, 25 g maltose, 825 mg $NH_4NO_3$, 750 mg glutamine, 690 mg proline, 500 mg casein hydrolysate, 100 mg inositol, 0.4 mg thiamine hydrochloride, 0.15 mg 2,4-dichlorophenoxyacetic acid (2,4-D), 5 mg kinetin, 1.25 mg $CuSO_4.5H_2O$, 3.4 g plant gel, and adjusted to pH=5.8 with 1 M NaOH;

the differentiation screening culture medium, including: the differentiation culture medium, 200 mg the mixture of ticarcillin and clavulanic acid (Timentin™), and 15 mg hygromycin;

c, the rooting culture medium, including: 4.3 g MS basic culture medium without vitamin, 30 g maltose, 1.0 g casein hydrolysate, 690 mg proline, 350 mg inositol, 1.0 mg thiamine hydrochloride, 3.2 g plant gel, and adjusted to pH=5.8 with 1 M NaOH; and the rooting screening culture medium, including: the rooting culture medium, 160 mg the mixture of ticarcillin and clavulanic acid (Timentin™), and 10 mg hygromycin.

During applications of the above culture media, a dosage of antibiotics is gradually reduced in the stages of the callus differentiation and the rooting induction culture under a condition of *Agrobacterium* transformation. The plant gel of the callus induction culture medium is autoclaved, the rest of the ingredients are filtered and sterilized, and the differentiation and rooting culture media are autoclaved.

In an embodiment, in the step S4, primers used in the performing DNA extraction and PCR detection on the obtained tissue culture plantlets, include:

Cas9-F, consisting of the nucleotide sequence shown as SEQ ID NO: 1; and

Cas9-R, consisting of the nucleotide sequence shown as SEQ ID NO: 2.

In an embodiment, during performing the PCR amplification on a sequence near a target of each of the positive plantlets, and detecting the mutation sites by Sanger sequencing in the step S4, a sequencing primer is hmsos1sg1F consisting of the nucleotide sequence shown as SEQ ID NO: 4 in the step S4.

In an embodiment, the immature embryo materials of sea barleygrass are selected from field or net room cultivated plants, growth states of the immature embryos growing in a natural environment are consistent, the materials are convenient to obtain, and the regeneration activity is strong. The immature spike materials of sea barleygrass in an artificial climate room are easy to breed pathogens, so that they must be thoroughly sterilized.

In an embodiment, a concentration of *Agrobacterium* liquid infecting the immature embryos is strictly controlled at $OD_{600}$=0.5-0.6, which is not required to be shaken and used immediately. The *Agrobacterium* liquid can be reused if it is stored at 4° C. in the dark for 2 days and kept at the above concentration, but it should be ensured that the *Agrobacterium* liquid is not contaminated by miscellaneous bacteria. When using a pipettor to add the *Agrobacterium* liquid to the middles of the immature embryos, be careful not to drop too much. When the *Agrobacterium* liquid completely wraps the immature embryos, the excess *Agrobacterium* liquid would be sucked back to avoid excessive residual *Agrobacterium* liquid causing excessive subsequent *Agrobacterium*. When the *Agrobacterium* liquid sucked each time is consumed, pay attention to replacing a new sterilization suction head to avoid cross contamination of the immature embryos.

In an embodiment, a dosage of hygromycin kept an initial dosage in the stage of the callus induction, which is conducive to the screening of positive calli. However, the dosage should be gradually reduced in the stage of the callus differentiation, especially in the stage of the rooting induction culture. On the basis of ensuring the positive plantlets, it is beneficial to shorten the time of plantlet formation and rooting.

Compared with the prior art, the disclosure has beneficial effects as follows.

1. The immature embryos are used as explants, a tissue culture regeneration system of sea barleygrass is established for the first time, with high green spot differentiation and plantlet formation rate.

2. The tissue culture system provided by the disclosure is generally applicable to different sea barleygrass materials.

3. The *Agrobacterium*-mediated genetic transformation system of sea barleygrass is provided, which have a high transformation efficiency and a gene editing efficiency. Transgenic sea barleygrass plants (mutants) are obtained, which can be applied to basic research such as gene function analysis of sea barleygrass.

BRIEF DESCRIPTION OF DRAWINGS

FIG. 5 is an agarose gel electrophoresis diagram of positive plantlets identified by a polymerase chain reaction (PCR) molecular detection method in embodiment 2, where a primer amplification length is 572 base pairs (bp), a first lane is a DL5000 marker indicating that a band is located at a designated position between 500 bp and 750 bp; a second lane is a positive control, that is, a fragment of primer amplification vector pUB-Cas9-U6-HmSOS1sgRNA01, revealing a location of a target band and primer specificity; a third lane is a negative control, that is, a wild-type H559 DNA as a template is amplified not obtaining the target band; L1-L23 at a beginning of a fourth lane in each row represented 23 regenerated plantlets obtained by transformation, a total of 19 strains with positive bands are detected, and a positive rate is 82.6%.

DETAILED DESCRIPTION OF EMBODIMENTS

Technical solutions of the disclosure will be further described in detail below in combination with specific embodiments. It should be understood that implementations of the disclosure may be realized in many different forms, not limited to the embodiments described herein, and any variations and/or changes in the forms of the disclosure are intended to fall within the protection scope of the disclosure.

In the disclosure, unless otherwise specified, all parts and percentages are weight units, and equipment and raw materials used can be purchased from markets or commonly used in the art. Unless otherwise specified, methods in the following embodiments are conventional methods in the art.

Sources of related reagents and drugs are:

Murashige and Skoog (MS) basic culture medium without vitamin, purchased from PhytoTech (M524) in the United States;

MS culture medium without ammonium nitrate ($NH_4NO_3$) and vitamin, purchased from Beijing Coolaber (PM1090);

Dicamba ($C_8H_6Cl_2O_3$), purchased from Sigma-Aldrich (D5417);

2, 4-D (also referred to as 2,4-dichlorophenoxyacetic acid, $C_8H_6O_3Cl_2$), purchased from Sigma-Aldrich (D7299);

Kinetin, purchased from Sigma-Aldrich (K3378);

Hygromycin, purchased from Sangon Biotech (Shanghai) Co., Ltd. (B540725);

Timentin™ (also referred to as ticarcillin/clavulanate potassium, which is a mixture of ticarcillin and clavulanic acid), purchased from Sangon Biotech (Shanghai) Co., Ltd. (A600950);

Plant gel (also referred to as Phytagel™), purchased from Sigma-Aldrich (P8169);

The rest of the drugs and reagents are purchased from Sangon Biotech (Shanghai) Co., Ltd.; and Agrobacterium AGL1 chemical transformation competent state (also referred to as AGL1 chemically competent cell) (CAT #: AC1020), purchased from Shanghai Weidi Biotechnology Co., Ltd.

Embodiment 1: Acquisition of Tissue Culture Regenerated Plantlets of Sea Barleygrass marinum Subspecies Accessions 11508, 11559, 11560 and 11761

1. selection and sterilization of immature embryo materials of sea barleygrass. Specifically, immature spikes of sea barleygrass marinum subspecies accessions H508, H559, H560 and H761 cultivated in a field natural environment (Trial A) and an artificial environment (Trial B) are taken, and then immature embryo materials of the immature sea barleygrass with plump seeds, gelatinous endosperm, and translucent immature embryos each having 0.5-1.0 millimeters (mm) in length are selected. Awns of the selected immature embryo materials are retained and immature embryo seed coats are kept to be intact. The immature embryo materials are collected and placed in a sterile 50 milliliters (mL) centrifuge tube with a volume of up to 20 mL. The above seeds are sterilized on a clean bench, and operations are as follows: adding 40 mL of 70% alcohol, turning upside down for 30 seconds (s), rinsing with sterilized water for 3 times, then adding 40 mL of 50% (v/v, i.e., volume per volume) sodium hypochlorite solution freshly prepared, standing for 2 minutes (min), rinsing with sterilized water for 2 times, adding 40 mL of 50% (v/v) sodium hypochlorite solution freshly prepared again, standing for 3 min, and rinsing repeatedly with sterilized water for 5 times to thereby obtain sterilized seeds.

Figure 1:
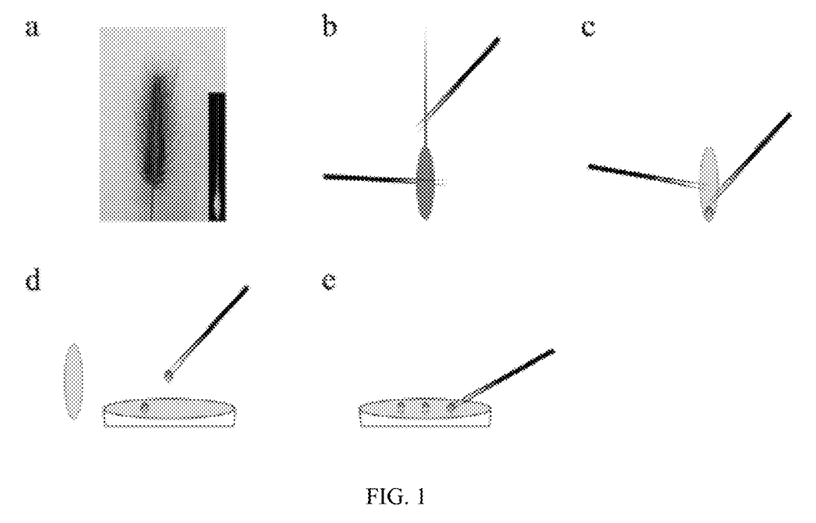
FIG. 1a is a schematic diagram of an immature spike of sea barleygrass and an immature embryo material after a preliminary treatment.
FIG. 1b is a schematic diagram showing that tips of a pair of left-hand tweezers clamp a seed, and tips of a pair of right-hand tweezers tear the awn to pull off an entire back seed coat to thereby expose an entire immature embryo.
FIG. 1c is a schematic diagram showing that the tips of the pair of left-hand tweezers pierce ½ of an endosperm and fixe the seed without the entire back seed coat, the tips of the pair of right-hand tweezers obliquely press an upper of the endosperm of the immature embryo to peel off the whole immature embryo.
FIG. 1d is a schematic diagram showing that the whole immature embryo is placed on a surface of a callus induction culture medium with a front face upward.
FIG. 1e is a schematic diagram showing that middles of peeled-off immature embryos are crosscut one by one with tips of one of the pair of left-hand tweezers and the pair of right-hand tweezers.
Figure 2:
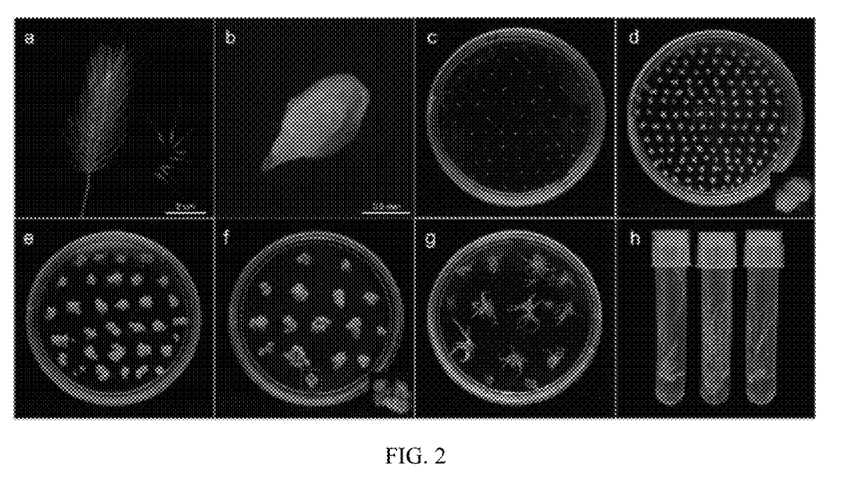
FIG. 2a is a schematic diagram showing that the immature spike of sea barleygrass and the immature embryo materials with aborted spikelets removed on both sides.
FIG. 2b is a schematic diagram showing that a peeled-off immature embryo.
FIG. 2c is a schematic diagram showing immature embryo induction culture on a first day of dark culture.
FIG. 2d is a schematic diagram showing that callus induction (screening) culture and proliferation cultured in dark for 21 days.
FIG. 2e is a schematic diagram showing that callus induction (screening) culture cultured in dark for 60 days.
FIG. 2f is a schematic diagram showing that green spot formation and bud induction and differentiation cultured in low light for 14 days.
FIG. 2g is a schematic diagram showing that differentiation and (screening) culture of adventitious buds cultured in low light for 30 days.
FIG. 2h is a schematic diagram showing that generating plantlets and rooting (screening) culture.
Figure 3:
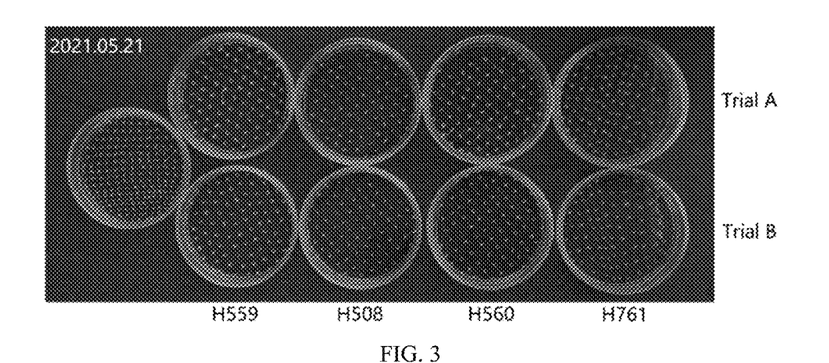
FIG. 3 is a schematic diagram showing that a growth of peeled-off immature embryos of sea barleygrass *marinum* subspecies accessions H508, H559, H560 and H761 cultivated in a field natural environment (Trial A) and an artificial environment (Trial B) in embodiment 1.

2. separation and callus induction of the immature embryos (as shown in FIG. 1 and FIG. 2). Specifically, the sterilized seeds (i.e., sterilized immature embryo materials) in the above step are taken and placed on a petri dish covered with a double-layer sterile filter paper, and a back of each of the sterilized seeds faces up and a tail of each awn faces away from an operator. For each of the sterilized seeds, tips of a pair of left-hand tweezers clamp the sterilized seed, and tips of a pair of right-hand tweezers tear the awn and peel off the entire back seed coat to expose the immature embryo entirely. The tips of the pair of left-hand tweezers pierce ½ of an endosperm of the exposed immature embryo and fix the sterilized seed without the entire back seed coat, the tips of the pair of right-hand tweezers obliquely press an upper of the endosperm of the immature embryo to thereby peel off a complete immature embryo, to thereby obtain peeled-off immature embryos. The peeled-off immature embryos are placed on a surface of a callus induction culture medium gently with fronts face upward, specifically, 80 peeled-off immature embryos may be placed in each petri dish, and middles of the peeled-off immature embryos are crosscut one by one with the tips of the pair of tweezers (as shown in FIG. 3). After crosscut immature embryos are cultured in dark at 22 Celsius degrees (° C.) for 7 days, minor seedling buds are removed with the tips of the pair of tweezers, and then dark culture is performed for another 7 days, and seedling buds and soft non-embryonic calli are removed. After changing a new callus induction culture medium, callus culture is performed in the dark for 2 weeks. Yellow and dense embryogenic calli are taken, 20 calli are placed in each petri dish, and the calli are cultured in the dark at 22° C. for 4 weeks, the callus induction culture medium without hygromycin and the mixture of ticarcillin and clavulanic acid (Timentin™) is replaced every two weeks.

3. callus differentiation and plantlet formation (as shown in FIG. 2). Specifically, since the calli are exposed to light, the petri dish cover and a culture tube cover are covered with single-layer A4 sized papers throughout in stages of the callus differentiation and the rooting induction culture to create a shielding-formed low-light environment. Yellow and dense callus blocks obtained from the step 2 are taken first, 15 numbers of individual callus blocks per petri dish is appropriate, and the individual callus blocks are placed in a differentiation culture medium to be cultured for 2 weeks under the shielding-formed low-light environment. Whitish parts and soft texture of callus blocks are removed, and small callus blocks with differentiated green spots are selected and transferred to a new differentiation (screening) culture medium for 3 weeks under the shielding-formed low-light environment. When the differentiated green spots become plantlets and grow to 2-3 centimeters (cm), the plantlets are transferred to 12 mL shaker tube (2 mL culture medium) containing a rooting (screening) culture medium, and root systems are established after 3 weeks of culture. When refining the plantlets, the tube cover is opened, sterilized water is added to 1 cm above a liquid level, the plantlets are adapted to an external environment for 2 days, the rooting (screening) culture medium around the roots are rinsed with tap water, and the rinsed plantlets are cultured in ⅕ Hogland barley hydroponic nutrient solution (also referred to as Hogland solution, or Hogland hydroponic culture medium) for 2 weeks and then bred in soil.

4. Preparation of the culture media in advance according to steps 2-3.

Specifically, preparation steps of the callus induction culture medium are as follows: preparing 2× plant gel at 121° C. for 20 min, and autoclaving; adding other medium components at 2× concentration, dissolving, adjusting pH=5.8 with 1 Mole per liter (M) sodium hydroxide (NaOH), and sterilizing with a filter; adding 2× plant gel and 2× medium components in a 65° C. water bath and heating for 20 min; mixing 2× plant gel and 2× medium composition; adding hormone and/or antibiotic storage solution (1000×) on a clean bench and shaking well to thereby obtain a mixed solution; and measuring and pouring 20 mL the mixed solution into a sterile petri dish with a diameter of 9 cm by using a 50 mL sterile centrifuge tube.

Preparation steps of a differentiation culture medium and a rooting culture medium are as follows: weighing medium components (including plant gel) and dissolving the weighed medium components in a beaker, making up to volume, adjusting 1 M NaOH to pH=5.8, and autoclaving; adding hormone and antibiotic storage solution (1000×) on the clean bench and shaking well thereby obtain a mixture solution; and measuring and pouring 20 mL the mixture solution into another sterile petri dish with a diameter of 9 cm by using another 50 mL sterile centrifuge tube. For the rooting culture medium, 2 mL of culture medium is pipetted with a 5 mL pipettor into a 12 mL shaker tube.

Reagents and hormones to be added are as follows (1 L).

a, the callus induction culture medium, including: grams (g) MS culture medium without vitamin, 30 g maltose, 1.0 g casein hydrolysate, 690 micrograms (mg) proline, 350 mg inositol, 1.0 mg thiamine hydrochloride, 5 mg dicamba, 1.25 mg copper sulfate pentahydrate ($CuSO_4 \cdot 5H_2O$), 3.65 g plant gel; if the callus induction screening culture medium is prepared, 200 mg the mixture of ticarcillin and clavulanic acid (Timentin™) and 25 mg hygromycin should be added on a basis of a, which should be adjusted to pH=5.8 with 1 M NaOH.

b. the differentiation culture medium, including: 2.7 g MS culture medium without $NH_4NO_3$ and vitamin, 25 g maltose, 825 mg $NH_4NO_3$, 750 mg glutamine, 690 mg proline, 500 mg casein hydrolysate, 100 mg inositol, 0.4 mg thiamine hydrochloride, 0.15 mg 2,4-D, 5 mg kinetin, 1.25 mg $CuSO_4 \cdot 5H_2O$, 3.4 g plant gel; if the differentiation screening culture medium is prepared, 200 mg the mixture of ticarcillin and clavulanic acid (Timentin™) and 15 mg hygromycin should be added on a basis of b, which should be adjusted to pH=5.8 with 1 M NaOH.

c, the rooting culture medium, including: 4.3 g MS culture medium without vitamin, 30 g maltose, 1.0 g casein hydrolysate, 690 mg proline, 350 mg inositol, 1.0 mg thiamine hydrochloride, 3.2 g plant gel; if the rooting screening culture medium is prepared, 160 mg the mixture of ticarcillin and clavulanic acid (Timentin™) and 10 mg hygromycin should be added on a basis of c, which should be adjusted to pH=5.8 with 1 M NaOH.

Figure 4:
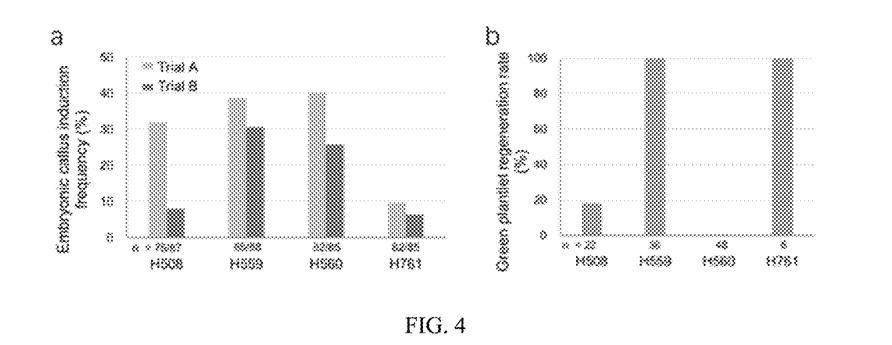
FIG. 4a is a schematic diagram showing that embryogenic callus induction rates (also referred to as embryonic callus induction frequencies) of the immature embryos of four materials of sea barleygrass marinum subspecies accessions H508, H559, H560 and H761 cultivated in the field natural environment (Trial A) and the artificial environment (Trial B).
FIG. 4b is a schematic diagram showing that green plantlet regeneration rates (also referred to as green spot regeneration rates) of the four materials cultured in low light for 30 days.

75, 85, 82 and 82 immature embryos initially peeled from the sea barleygrass *marinum* subspecies accessions H508, H559, H560, and H761 cultivated under the field natural environment (Trial A) are performed with callus induction, and cultured for 30 days. After removal of necrotic immature embryos such as miscellaneous bacteria pollution and callus death, 24, 33, 33 and 8 complete embryogenic calli are obtained respectively, and callus induction differentiation rates (also referred to as embryonic callus induction frequencies) are about 32.0%, 38.8%, 40.2% and 9.6% respectively. 87, 88, 85 and 85 initially peeled from the sea barleygrass *marinum* subspecies accessions H508, H559, H560, and H761 cultivated under the artificial environment (Trial B) are performed with callus induction, and cultured for 30 days. After removal of necrotic immature embryos such as miscellaneous bacteria pollution and callus death, 7, 25, 21 and 6 complete embryogenic calli are obtained respectively, and callus induction differentiation rates are about 8.0%, 30.7%, 25.9% and 6.5% (as shown in FIG. 4a). The results showed that the immature embryo materials of sea barleygrass cultivated under the field natural environment have a stronger regeneration activity than those under the artificial environment.

22, 36, 48 and 8 complete embryogenic calli induced by immature embryos of H508, H559, H560, and H761 are used for differentiation culture. Green plantlet differentiation rates (also referred to as green spot differentiation rates) are about 18.2%, 100%, 0% and 100% respectively (as shown in FIG. 4b). Final plantlets are 21, 73, 0 and 36 respectively, indicating that the immature embryos of sea barleygrass accessions H508, H559, H560, and H761 have the strong regeneration activity.

According to the above results of the callus induction rates and the green plantlet regeneration rates, the tissue culture system is efficient and widely applicable to different materials of sea barleygrass, and the *marinum* subspecies accession H559 is the preferred material.

Embodiment 2: *Agrobacterium*-Mediated Genetic Transformation of Immature Embryos of Sea Barleygrass Accession 11559 to Obtain Mutant Plants 1. selection and sterilization of immature embryo materials of sea barleygrass. Specifically, immature spikes of sea barleygrass *marinum* subspecies accession H559 cultivated in an artificial environment are taken, then immature embryo materials of the immature sea barleygrass with plump seeds, gelatinous endosperm, and translucent immature embryos each having a length in a range of 0.5-1.0 mm are selected. Awns of the selected immature embryo materials are retained and immature embryo seed coats are kept to be intact. The immature embryo materials are collected and placed in a sterile 50 mL centrifuge tube with a volume of up to 20 mL. The above seeds are sterilized on a clean bench, and operations are as follows: adding 40 mL of 70% alcohol, turning upside down for 30 s, rinsing with sterilized water for 3 times, then adding 40 mL of 50% (v/v) sodium hypochlorite solution freshly prepared, standing for 2 min, rinsing with sterilized water for 2 times, adding 40 mL of 50% (v/v) sodium hypochlorite solution freshly prepared again, standing for 3 min, and rinsing repeatedly with sterilized water for 5 times to thereby obtain sterilized seeds.

2. separation and callus induction of immature embryos (as shown in FIG. 1 and FIG. 2). Specifically, the sterilized seeds in the above step are taken and placed on a petri dish covered with a double-layer sterile filter paper, and a back of each of the sterilized seeds faces up and a tail of each awn faces away from an operator. For each of the sterilized seeds, tips of a pair of left-hand tweezers clamp the sterilized seed, and tips of a pair of right-hand tweezers tear the awn and peel off the entire back seed coat to expose the immature embryo entirely. The tips of the pair of left-hand tweezers pierce ½ of an endosperm of the immature embryo and fix the sterilized seed without the entire back seed coat, the tips of the pair of right-hand tweezers obliquely press an upper of the endosperm of the immature embryo to thereby peel off a complete immature embryo, to thereby obtain peeled-off immature embryos. The peeled-off immature embryos are placed on a surface of a callus induction culture medium gently with fronts face upward, specifically, 80 peeled-off immature embryos may be placed in each petri dish, and middles of the peeled-off immature embryos are crosscut one by one with the tips of the pair of tweezers (as shown in FIG. 3). After crosscut immature embryos are cultured in dark at 22° C. for 7 days, minor seedling buds are removed with the tips of the pair of tweezers, and then callus culture is performed in dark for another 7 days, and seedling buds and soft non-embryonic calli are removed. After changing a new callus induction culture medium, callus culture is performed in dark for 2 weeks.

3. *Agrobacterium* infection and selective culture. Specifically, yellow and dense embryogenic calli obtained from the step 2 and pre-cultured at 22° C. in the dark for 1 week. *Agrobacterium* liquid containing a target plasmid pUB-Cas9-U6-HmSOS1sgRNA01 (MG basic culture medium, without antibiotic, $OD_{600}$=0.5-0.6) is prepared in advance. Callus blocks with diameters in a range of 2-3 mm are taken, and a 20 microliters (µL) pipettor is used to suck the *Agrobacterium* liquid, and the *Agrobacterium* liquid is dropwise added in middles of the taken callus blocks to thereby wrap the whole callus blocks, and immediately suck back excess liquid. Each petri dish is slightly tilted on the clean bench, and replaced to a new callus induction culture medium after excess liquid is blown dry, where the number of calli per petri dish should be 40. After 36-48 hours of co-culture in the dark, the number of calli is reduced to 20 per petri dish, and two rounds of callus induction screening culture medium are replaced for 4 weeks of dark culture.

4. callus differentiation, plantlet formation and positive plantlet detection. Specifically, since the calli are exposed to light, the petri dish cover and a culture tube cover are covered with single-layer A4 sized papers throughout in stages of the callus differentiation and the rooting induction culture to create a shielding-formed low-light environment. Yellow and dense callus blocks from the callus blocks obtained from the step 3 are taken first, 15 numbers of individual callus blocks per petri dish is appropriate, and the individual callus blocks are placed in a differentiation culture medium to be cultured for 2 weeks under the shielding-formed low-light environment. Whitish parts and soft texture of callus blocks are removed, and small callus blocks with differentiated green spots are selected and transferred to a new differentiation (screening) culture medium for 3 weeks under the shielding-formed low-light environment. When the differentiated green spots become plantlets and grow to 2-3 centimeters (cm), the plantlets are transferred to 12 mL shaker tube (2 mL culture medium) containing a rooting (screening) culture medium, and root systems are established after 3 weeks of culture. When refining the plantlets, the tube cover is opened immediately, sterilized water is added to 1 cm above a liquid level, the plantlets are adapted to an external environment for 2 days, the rooting (screening) culture medium around the roots are rinsed with tap water, and the rinsed plantlets are cultured in ⅕ Hogland barley hydroponic nutrient solution for 2 weeks. DNA is extracted from some leaves, and transgenic target bands are detected by PCR. The primers used are as follows.

Cas9-F: CCTGGCCCACATGATCAAGT, and its nucleotide sequence is shown as SEQ ID NO: 1; and Cas9-R: TGTACTTCTCAGGCAGCTGC, and its nucleotide sequence is shown as SEQ ID NO: 2.

Whether it is a positive plantlet is determined. Specifically, PCR amplification is performed on a sequence near a positive plantlet target (GAAGACGGCCAGGAGGAGGT, and its nucleotide sequence is shown as SEQ ID NO: 3), and Sanger sequencing is used to detect mutation sites. A sequencing primer is as follows.

hmsos1sg1F: CCGGCATCCGCATCTGTA, its nucleotide sequence is shown in SEQ ID NO: 4.

The mutants are propagated in soil culture for subsequent studies.

5. The preparation of the culture media are described in the step 4 of the embodiment 1.

Figure 5:
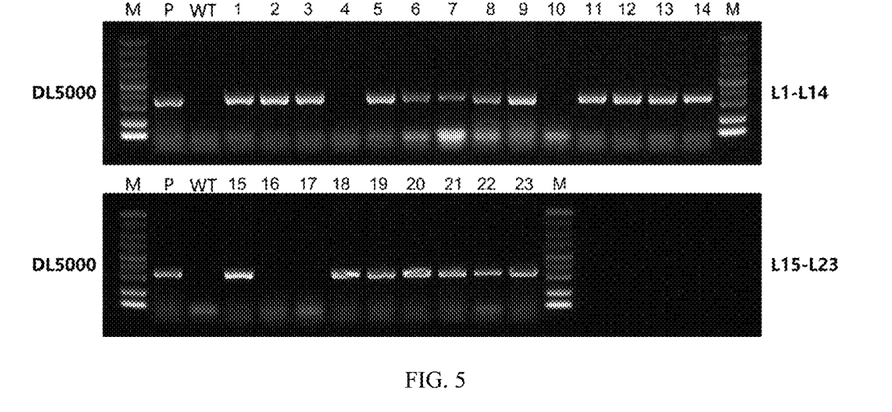
Figure 6:
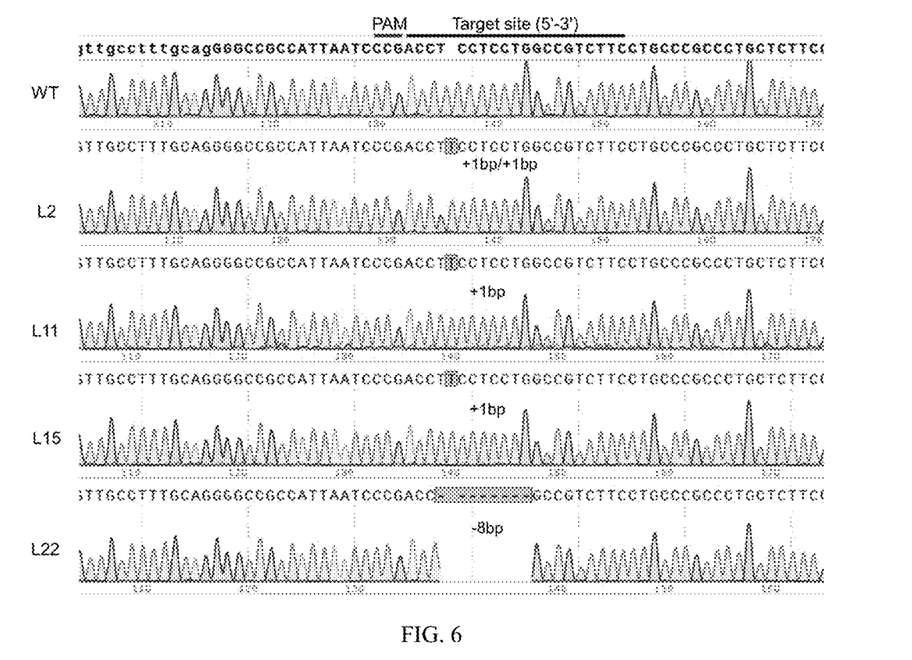
FIG. 6 shows a comparison result of sequencing peak diagram of sequences near a target of homozygous mutants in the positive plantlets obtained in the embodiment 2, indicating that 19 positive plantlets include 1 biallelic mutant (including L2 with the nucleotide sequence as shown in SEQ ID NO: 6) and 3 homozygous mutants (including L11, L15 and L22 with the nucleotide sequences respectively as shown in SEQ ID NO: 7-9).

236 immature embryos initially peeled from sea barleygrass accession H559 are performed with callus induction. After removing necrotic immature embryos such as excessive bacterial liquid, miscellaneous bacteria pollution, and callus death, 43 complete calli are left at the light stage, and the green plantlet differentiation rate reached 100%. Finally, 23 regenerated plantlets are obtained. Genomic DNA is extracted for PCR identification, a total of 19 positive plantlets are detected, with a positive rate of 82.6% (as shown in FIG. 5). PCR amplification and Sanger sequencing are performed on the sequences near the target sites of all positive plantlets. The results of peak diagram comparison show that 19 positive plantlets included 1 biallelic mutant (i.e., L2) and 3 homozygous mutants (i.e., L11, L15 and L22), and the rest are heterozygous mutations, with editing efficiency up to 100% (as shown in FIG. 6).

As shown in FIG. 5, a primer amplification length is 572 base pairs (bp), a first lane is a DL5000 marker indicating that a band is located at a designated position between 500 bp and 750 bp; a second lane is a positive control, that is, a fragment of primer amplification vector pUB-Cas9-U6-HmSOS1sgRNA01, revealing a location of a target band and primer specificity; a third lane is a negative control, that is, a wild-type H559 DNA (with the nucleotide sequence as shown in SEQ ID NO: 5) as a template is amplified not obtaining the target band; L1-L23 at a beginning of a fourth lane in each row represented 23 regenerated plantlets obtained by transformation, a total of 19 strains with positive bands are detected, and a positive rate is 82.6%. From this, the initial number of immature embryos required to obtain 10 positive strains is estimated to be about 100. FIG. 6 illustrates a comparison result of sequencing peak diagram of sequences near a target of the positive plantlets, indicating that 19 positive plantlets include 1 biallelic mutant (i.e., L2 with the nucleotide sequence as shown in SEQ ID NO: 6) and 3 homozygous mutants (i.e., L11, L15 and L22 with the nucleotide sequences respectively as shown in SEQ ID NO: 7-9). The other strains are heterozygous mutations, and the editing efficiency is 100%.

It can be seen from experimental results of the above two embodiments that tissue culture method and genetic transformation system of sea barleygrass provided by the disclosure have high efficiency and universality, high transformation efficiency and gene editing efficiency, and can be applied to the study of gene function of sea barleygrass.

Finally, it should be noted that the above description is only a few specific embodiments of the disclosure, and is not intended to limit the disclosure in any form. Any simple variations, changes, and modification of the above embodiments according to the technical essence of the disclosure should be considered as the protection scope of the disclosure.

What is claimed is:

1. An *Agrobacterium*-mediated genetic transformation method for sea barleygrass, comprising:
    step S1, selection and sterilization of immature embryo materials of sea barleygrass, which comprises: selecting the immature embryo materials of sea barleygrass with immature embryos each having a length in a range of 0.5-1.0 millimeters (mm), and sterilizing selected immature embryo materials with alcohol and sodium hypochlorite to obtain sterilized seeds;
    step S2, separation and callus induction of the immature embryos, which comprises: separating the immature embryos from the sterilized seeds, crosscutting the immature embryos, and inducing callus generation and proliferation, thereby obtaining calli;
    step S3, *Agrobacterium* infection and selective culture, which comprises: adjusting pre-culture time and *Agrobacterium* infection time of the calli based on the callus generation and *Agrobacterium* growth to thereby prevent excessive *Agrobacterium* liquid; wherein a culture medium for the selective culture is added with a mixture of ticarcillin and clavulanic acid and hygromycin; and
    step S4, callus differentiation, plantlet formation, and positive plantlet detection, which comprises: performing adventitious bud induction culture and rooting induction culture under a shielding-formed low-light environment to thereby obtain tissue culture plantlets, and then performing deoxyribonucleic acid (DNA) extraction and polymerase chain reaction (PCR) detection on obtained tissue culture plantlets to obtain PCR detection results, and determining whether target fragments are amplified based on the PCR detection results, to thereby determine whether the tissue culture plantlets are positive plantlets; wherein an *Agrobacterium tumefaciens* recombinant strain used for transformation carries a gene editing vector, further comprising performing PCR amplification on a sequence near a target of each of the positive plantlets, and detecting mutation sites by Sanger sequencing, and a hmsos1sg1F sequencing primer consisting of the nucleotide sequence comprising SEQ ID NO: 4.

2. The method according to claim 1, wherein in the step S1, the selection and sterilization of immature embryo materials of sea barleygrass further comprises:
    selecting the immature embryo materials of sea barleygrass with plump seeds, gelatinous endosperms, and translucent immature embryos each having the length in the range of 0.5-1.0 mm, retaining awns and keeping seed coats of the immature embryo materials to be intact, sterilizing the immature embryo materials of sea barleygrass with 70% alcohol, then soaking sterilized immature embryo materials in a prepared sodium hypochlorite solution, and subsequently rinsing soaked immature embryo materials repeatedly with sterilized water, to thereby obtain the sterilized seeds.

3. The method according to claim 1, wherein in the step S2, the separation and callus induction of the immature embryos further comprises:
    taking the sterilized seeds obtained from the step S1, and placing taken sterilized seeds on a petri dish covered with a double-layer sterile filter paper, wherein a back of each of the sterilized seeds faces up and a tail of the awn faces away from an operator;
    using a clamping method with tips of double pairs of tweezers to pull off an entire back seed coat of each of the sterilized seeds to expose the immature embryo of each of the sterilized seeds, wherein tips of a pair of left-hand tweezers of the double pairs of tweezers clamp the sterilized seed, and tips of a pair of right-hand tweezers of the double pairs of tweezers tear the awn;
    piercing ½ of an endosperm of each of the exposed immature embryos with the tips of the pair of left-hand tweezers and fixing the sterilized seed without the entire back seed coat, and obliquely pressing an upper of the endosperm of the immature embryo with the tips of the pair of right-hand tweezers to peel off the immature embryo, to thereby obtain peeled-off immature embryos;
    placing the peeled-off immature embryos on a surface of a callus induction culture medium with fronts face upward, crosscutting middles of the peeled-off immature embryos one by one with the tips of one of the double pairs of tweezers; and culturing crosscut immature embryos in dark at 22° C. for 7 days, removing minor seedling buds with the tips of one of the double pairs of tweezers, continuing culturing in dark for 7 days, and then removing seedling buds and non-embryonic calli; and performing callus culture in dark for 2-3 weeks after replacing a new callus induction culture medium, to thereby obtain the calli;

wherein a subsequent operation is performed according to the step S3 when *Agrobacterium* infection is required to obtain transgenic plants;

wherein when the calli are directly used for the callus induction, yellow and dense embryogenic calli are taken from the calli obtain from the step S2 and cultured in dark at 22° C. for 3-4 weeks, a callus induction culture medium without hygromycin and the mixture of ticarcillin and clavulanic acid is replaced every two weeks, and then a subsequent operation is performed according to the step S4.

4. The method according to claim 1, wherein in the step S3, the *Agrobacterium* infection and selective culture further comprises:

taking yellow and dense embryogenic calli from the calli obtained from the step S2, and pre-culturing the taken yellow and dense embryogenic calli at 22° C. for 1 week, to thereby obtain pre-cultured callus blocks;

taking callus blocks each with a diameter of 2-3 mm from the pre-cultured callus blocks, using a 20 microliters (L) pipettor to suck *Agrobacterium* liquid, dropwise adding sucked *Agrobacterium* liquid in middles of taken callus blocks to wrap the taken callus blocks, then immediately sucking back excess *Agrobacterium* liquid, placing a petri dish in a tilted manner with the taken callus blocks on a clean bench in a tilted manner, and replacing a new callus induction culture medium after excess *Agrobacterium* liquid is dried, to thereby obtain infected callus blocks; and co-culturing the infected callus blocks for 36-48 hours, reducing a number of co-cultured callus blocks to 20-30 per petri dish, replacing two rounds of callus induction screening culture medium, and culturing in dark for 3-4 weeks, to thereby obtain final co-cultured callus blocks.

5. The method according to claim 4, wherein the *Agrobacterium* liquid employs a MG basic culture solution without antibiotic, and a concentration $OD_{600}$ (abbreviation for optical density at 600 nanometers) of the *Agrobacterium* liquid is in a range of 0.5-0.6.

6. The method according to claim 1, wherein in the step S4, the callus differentiation, plantlet formation, and positive plantlet detection further comprises:

covering a petri dish cover and a culture tube cover with single-layer A4 sized papers throughout in stages of the callus differentiation and the rooting induction culture since the calli are exposed to light, to thereby create the shielding-formed low-light environment;

taking yellow and dense callus blocks obtained in the step S2 or obtained in the step S3, 15-20 numbers of individual callus blocks per petri dish, and then culturing taken callus blocks for 2 weeks in a differentiation culture medium or a differentiation screening culture medium under the shielding-formed low-light environment;

removing whitish parts of callus blocks, selecting callus blocks with differentiated green spots, transferring selected callus blocks with the differentiated green spots to a new differentiation culture medium or a new differentiation screening culture medium, and then culturing for 2-4 weeks under the shielding-formed low-light environment;

when the differentiated green spots grow to be plantlets each with a length in a range of 2-3 centimeters (cm), transferring the plantlets to a rooting culture medium or a rooting screening culture medium, and then culturing for 2-3 weeks to form root systems of the plantlets;

when refining the plantlets, opening the culture tube cover, adding sterilized water to 1-2 cm above a liquid level, adapting to 1-2 days in an external environment, rinsing the rooting culture medium or the rooting screening culture around the root systems with tap water, and then culturing rinsed plantlets in a ⅕ Hoagland hydroponic culture medium for 3-4 weeks, to thereby obtain the tissue culture plantlets;

wherein the callus differentiation and the plantlet formation are performed after transformation, the differentiation screening culture medium and the rooting screening culture medium are used.

7. The method according to claim 1, wherein a dosage of the hygromycin maintains an initial dosage in a stage of the callus induction, and then is gradually reduced in a stage of the callus differentiation and in a stage of the rooting induction culture.

8. The method according to claim 3, wherein the callus induction culture medium in the step S2 using a Murashige and Skoog (MS) culture medium as a basic culture medium, and ingredients in 1 L (liter) comprise:

4.3 grams (g) of MS basic culture medium without vitamin, 30 g of maltose, 1.0 g of casein hydrolysate, 690 micrograms (mg) of proline, 350 mg of inositol, 1.0 mg of thiamine hydrochloride, 5 mg of dicamba, 1.25 mg of copper sulfate pentahydrate ($CuSO_4 \cdot 5H_2O$), 3.65 g of plant gel, and adjusted to pH=5.8 with 1 Mole per liter (M) sodium hydroxide (NaOH).

9. The method according to claim 4, wherein the callus induction culture medium in the step S3 using a MS culture medium as a basic culture medium, and ingredients in 1 L comprise:

4.3 g of MS basic culture medium without vitamin, 30 g of maltose, 1.0 g of casein hydrolysate, 690 mg of proline, 350 mg of inositol, 1.0 mg of thiamine hydrochloride, 5 mg of dicamba, 1.25 mg of $CuSO_4 \cdot 5H_2O$, 3.65 g of plant gel, and adjusted to pH=5.8 with 1 M NaOH;

wherein the callus induction screening culture medium in the step S3 comprises the callus induction culture medium, 200 mg of the mixture of ticarcillin and clavulanic acid, and 25 mg of hygromycin.

10. The method according to claim 6, wherein the differentiation culture medium in the step S4 using a MS culture medium as a basic culture medium, and ingredients in 1 L comprise:

2.7 g of MS basic culture medium without ammonium nitrate ($NH_4NO_3$) and vitamin, 25 g of maltose, 825 mg of $NH_4NO_3$, 750 mg of glutamine, 690 mg of proline, 500 mg of casein hydrolysate, 100 mg of inositol, 0.4 mg of thiamine hydrochloride, 0.15 mg of 2,4-dichlorophenoxyacetic acid (2,4-D), 5 mg of kinetin, 1.25 mg of $CuSO_4 \cdot 5H_2O$, 3.4 g of plant gel, and adjusted to pH=5.8 with 1 M NaOH;

wherein the differentiation screening culture medium in the step S4 comprises the differentiation culture medium, 200 mg of the mixture of ticarcillin and clavulanic acid, and 15 mg of hygromycin;

wherein the rooting culture medium in the step S4 comprises 4.3 g of MS basic culture medium without vitamin, 30 g of maltose, 1.0 g of casein hydrolysate, 690 mg of proline, 350 mg of inositol, 1.0 mg of thiamine hydrochloride, 3.2 g of plant gel, and adjusted to pH=5.8 with 1 M NaOH; and wherein the rooting screening culture medium in the step S4 comprises the rooting culture medium, 160 mg of the mixture of ticarcillin and clavulanic acid, and 10 mg of hygromycin.

11. The method according to claim 1, wherein in the step S4, primers used in the performing DNA extraction and PCR detection on obtained tissue culture plantlets, comprise:

Cas9-F, consisting of the nucleotide sequence comprising SEQ ID NO: 1; and

Cas9-R, consisting of the nucleotide sequence comprising SEQ ID NO: 2.

\* \* \* \* \*

```
                              SEQUENCE LISTING

Sequence total quantity: 9
SEQ ID NO: 1            moltype = DNA   length = 20
FEATURE                 Location/Qualifiers
misc_feature            1..20
                        note = Cas9-F
source                  1..20
                        mol_type = other DNA
                        organism = synthetic construct
SEQUENCE: 1
cctggcccac atgatcaagt                                                    20

SEQ ID NO: 2            moltype = DNA   length = 20
FEATURE                 Location/Qualifiers
misc_feature            1..20
                        note = Cas9-R
source                  1..20
                        mol_type = other DNA
                        organism = synthetic construct
SEQUENCE: 2
tgtacttctc aggcagctgc                                                    20

SEQ ID NO: 3            moltype = DNA   length = 20
FEATURE                 Location/Qualifiers
misc_feature            1..20
                        note = positive plantlet target
source                  1..20
                        mol_type = genomic DNA
                        organism = Hordeum marinum
SEQUENCE: 3
gaagacggcc aggaggaggt                                                    20

SEQ ID NO: 4            moltype = DNA   length = 18
FEATURE                 Location/Qualifiers
misc_feature            1..18
                        note = hmsos1sg1F
source                  1..18
                        mol_type = other DNA
                        organism = synthetic construct
SEQUENCE: 4
ccggcatccg catctgta                                                      18

SEQ ID NO: 5            moltype = DNA   length = 68
FEATURE                 Location/Qualifiers
source                  1..68
                        mol_type = genomic DNA
                        organism = Hordeum marinum
SEQUENCE: 5
ttgcctttgc aggggccgcc attaatcccg acctcctcct ggccgtcttc ctgcccgcc         60
tgctcttc                                                                 68

SEQ ID NO: 6            moltype = DNA   length = 69
FEATURE                 Location/Qualifiers
source                  1..69
                        mol_type = genomic DNA
                        organism = Hordeum marinum
SEQUENCE: 6
ttgcctttgc aggggccgcc attaatcccg accttcctcc tggccgtctt cctgcccgcc        60
ctgctcttc                                                                69

SEQ ID NO: 7            moltype = DNA   length = 69
```

```
                        -continued

FEATURE            Location/Qualifiers
source             1..69
                   mol_type = genomic DNA
                   organism = Hordeum marinum
SEQUENCE: 7
ttgcctttgc aggggccgcc attaatcccg accttcctcc tggccgtctt cctgcccgcc    60
ctgctcttc                                                            69

SEQ ID NO: 8       moltype = DNA  length = 69
FEATURE            Location/Qualifiers
source             1..69
                   mol_type = genomic DNA
                   organism = Hordeum marinum
SEQUENCE: 8
ttgcctttgc aggggccgcc attaatcccg accttcctcc tggccgtctt cctgcccgcc    60
ctgctcttc                                                            69

SEQ ID NO: 9       moltype = DNA  length = 60
FEATURE            Location/Qualifiers
source             1..60
                   mol_type = genomic DNA
                   organism = Hordeum marinum
SEQUENCE: 9
ttgcctttgc aggggccgcc attaatcccg accgccgtct tcctgcccgc cctgctcttc    60
```